United States Patent
Kasowski

(10) Patent No.: US 10,501,602 B2
(45) Date of Patent: Dec. 10, 2019

(54) FLAME RETARDANT AND FLAME RETARDANT USES

(71) Applicant: Robert Valentine Kasowski, West Chester, PA (US)

(72) Inventor: Robert Valentine Kasowski, West Chester, PA (US)

( * ) Notice: Subject to any disclaimer, the term of this patent is extended or adjusted under 35 U.S.C. 154(b) by 0 days.

(21) Appl. No.: 15/323,960

(22) PCT Filed: Dec. 12, 2015

(86) PCT No.: PCT/US2015/065415
§ 371 (c)(1),
(2) Date: Jan. 4, 2017

(87) PCT Pub. No.: WO2016/094887
PCT Pub. Date: Jun. 16, 2016

(65) Prior Publication Data
US 2017/0204250 A1    Jul. 20, 2017

(51) Int. Cl.
| | | |
|---|---|---|
| *C07F 9/38* | (2006.01) | |
| *C08K 5/521* | (2006.01) | |
| *C08K 7/02* | (2006.01) | |
| *A62C 3/02* | (2006.01) | |
| *C07F 9/09* | (2006.01) | |
| *C07C 209/68* | (2006.01) | |
| *C07C 211/10* | (2006.01) | |
| *D06M 13/322* | (2006.01) | |

(52) U.S. Cl.
CPC ............ *C08K 5/521* (2013.01); *A62C 3/0278* (2013.01); *C07C 209/68* (2013.01); *C07C 211/10* (2013.01); *C07F 9/09* (2013.01); *C07F 9/3873* (2013.01); *C08K 7/02* (2013.01); *D06M 13/322* (2013.01)

(58) Field of Classification Search
None
See application file for complete search history.

(56) References Cited

U.S. PATENT DOCUMENTS

| | | | | |
|---|---|---|---|---|
| 4,599,375 A * | 7/1986 | Berte' | .................... | C08K 13/02 524/100 |
| 7,115,677 B2 * | 10/2006 | Harashina | .............. | C08K 3/016 523/205 |
| 7,138,443 B2 * | 11/2006 | Kasowski | .......... | C08K 5/34922 523/179 |
| 8,212,073 B2 * | 7/2012 | Kasowski | .......... | C07D 295/027 252/609 |
| 8,703,853 B2 * | 4/2014 | Kasowski | ................. | C07F 9/02 524/148 |
| 2006/0175587 A1 * | 8/2006 | Kasowski | ................. | C07F 9/09 252/601 |
| 2013/0244527 A1 * | 9/2013 | Sarzotti | .................... | D01F 1/07 442/401 |
| 2013/0341575 A1 * | 12/2013 | Kasowski | .............. | C09K 21/12 252/601 |

* cited by examiner

*Primary Examiner* — Joseph D Anthony

(57) ABSTRACT

The flame-retardants of this invention were formed by the direct reaction of ethyleneamines and commercial polyphosphoric acid at an elevated temperature. It was unexpected that a high temperature had to be used to overcome reaction barrier to formation. These compounds are found to be efficient flame retardants.

12 Claims, No Drawings

FLAME RETARDANT AND FLAME RETARDANT USES

FIELD OF INVENTION

This invention relates to the formation of anhydrous flame retardant compositions and flame retardant containing compositions with commercial polyphosphoric acid, solvent free, for plastics and wildfires.

BACKGROUND OF INVENTION

In U.S. Pat. Nos. 7,138,443; 8,212,073; 8,703,853 and US application No. 2006/0175587 and PCT/US12/000247, all of which are incorporated herein by reference, ethyleneamine polyphosphates (EAPPA) are made from polyphosphoric acid (PPA) that was made by an ion exchange process because sodium polyphosphate has high molecular weight. In U.S. Pat. No. 7,138,443, it is specifically stated that it is preferred to make ethyleneamine polyphosphates with PPA from ion exchange process and not to use commercial polyphosphoric acid, which has much lower molecular weight. In US application No. 2006/0175587 (PCT/US2003/017268), with an international filing date of 3 Jun. 2003, Maya Kasowski shows that flame retardant diethylenetriamine polyphosphate (DETAPPA) compositions made with ion exchange have much better thermal stability that with commercial polyphosphoric acid, DETA, and water. It was stated explicitly that diethylenetriamine polyphosphate (DETAPPA) made with commercial PPA, DETA, and water could not be used above 250° C. in an extruder and thus is not suitable for mixing with nylon 66. It was also shown that DETAPPA with a pH of 5.3 ran poorly when mixed into polypropylene but DETAPPA with a pH of about 3.2 ran well with PP.

Syrup (approximately 60% EAPPA, 40% water) has a density of about 1.44 and separates to bottom of reaction vessel. EAPPA make with commercial PPA in these earlier references was not found to result in syrup when dissolved in water. One of the claims in U.S. Pat. No. 8,703,853 is that dehydration of the flame retardant syrup results in ethyleneamine polyphosphate with the property that when 3 g are dissolved in 20 ml water, at least 1.5 ml of syrup forms with a clear interface with the non-viscous phase. The formation of syrup was presented to be indicative of high molecular weight EAPPA, high thermal stability, and the best performance in an extruder. The ion exchange process used sodium polyphosphate with average chain length at least 11 suggesting such a molecular weight. Formation of syrup was associated with the highest quality EAPPA in terms of thermal stability, which will be shown to be inadequate criteria.

Such behavior does not occur when commercial polyphosphoric acid is used according to U.S. Pat. No. 8,212,073. In U.S. Pat. No. 8,212,073, it is specifically stated that "Syrup was only formed when an ethyleneamine such as EDA, DETA, TETA, and PEHA were reacted with ion exchange prepared polyphosphoric acid. The syrup did not form when commercial polyphosphoric acid was reacted with an ethyleneamine. Syrup also does not reform. For example, dry the syrup to form a flame retardant composition. Re-dissolve the flame retardant composition in water and the syrup phase does not separate." In U.S. Pat. No. 8,703,853, it is stated that ion exchange is the preferred process to make ethyleneamine polyphosphates. However, the EAPPA from the ion exchange process suffered a significant reduction in pH during drying of the syrup. Syrup with pH 5 was found to be reduced to a pH of about 3.5 by drying. IX process has substantial waste stream.

SUMMARY OF INVENTION

The first part of the invention is formation of anhydrous ethyleneamine polyphosphate (EAPPA) for the first time by direct reaction of ethyleneamine and commercial polyphosphoric acid (PPA) near the theoretical acid base ratio with the reaction performed without water or other solvent. This form of EAPPA can be made by reacting any grade of PPA with EA. The method requires that the equipment contain the reaction and that the product, depending on PPA grade, be broken up as the reaction forms and that the temperature be high enough so that intermediate EAPPA, usually of low pH, melts and mixes with remaining PPA and EA so that the reaction is completed and uniform. DETAPPA made with high molecular weight grade PPA115% or PPA117% when dissolved in water resulted in substantial syrup, an unexpected result. Previously in U.S. Pat. Nos. 8,212,073 and 8,703,853, EAPPA dissolved in water did not form syrup unless it had been subjected to molecular weight enhancement via condensation. DETAPPA made with PPA 117% was found to form at least 1.5 ml syrup per 3 g DETAPPA/10 g water and PPA 115% formed at least 3 ml syrup per 4 g DETAPPA/10 g water. DETAPPA made with PPA 105% did not form syrup when dissolved in water. It was further unexpected that DETAPPA that forms substantial syrup when dissolved in water did not extrude adequately into high temperature polymers such as nylon 66, indicating that formation of syrup is not an adequate indicator of high temperature performance. DETAPPA made with ion exchange method in U.S. Pat. No. 8,703,853 was judged to be applicable for nylon extrusion if syrup formed when dissolved in water. It has thus been shown that EA and PPA can be reacted to completion in a closed system without dangerous side reactions directly despite the large amount of heat generated in this incredibly fast, exothermic reaction. It was unexpected that the heat is actually helpful and necessary to keep the intermediate products melted so that the reaction completes. It is preferred that the absence of moisture be maintained with an inert environment as water would need to be removed during drying/condensation if used for plastics extrusion. Firefighting applications can tolerate moisture.

In the second part of this invention, EAPPA is converted by condensation to higher molecular weight so that its thermal stability becomes sufficiently high to be added via extrusion to engineering polymers such as nylon 66 and to be stickier for firefighting. All EAPPA formed from EA and PPA contain considerable amounts of ortho and pyro phosphate. It is preferred to remove or at least reduce such content by condensation to higher molecular weight resulting in a new composition of condensed EAPPA. Weight loss during condensation is greatest for EAPPA compositions made with PPA 105% at about 6% and least for PPA 117% at less than 0.5%. The condensed form of EAPPA is superior and different from that made via ion exchange in being sodium contamination free and contains the correct ratio of EA to PPA, but still having the very high thermal stability of the ion exchange made EAPPA. It is unexpected that changing EA/PPA ratio has little effect on thermal stability.

It was unexpected that PPA 105% with the approximate composition ortho (54%), pyrophosphoric (41%) and 5% triphosphoric could result in an EAPPA product of very high quality by subjecting to condensation.

One method of condensation consists of heating in vacuum at a temperature of at least 200° C. and as high as 250° C. so that water is extracted from PPA and higher molecular weight EAPPA results. The EAPPA condensation is often carried out for 60 minutes, depending on vacuum intensity. Any method of molecular weight enhancement that results in condensation is acceptable, for example thin film dehydration.

The ratio of EA to polyphosphoric acid distinguishes this new form of EAPPA from that formed by ion exchange method in U.S. Pat. No. 8,212,073. The ratio of diethylenetriamine to polyphosphoric acid is approximately 0.5 pounds of DETA per pound of commercial polyphosphoric acid for a pH of about 4, and the ratio is independent of grade of PPA. This is consistent with the findings of Masson for bitumen polyphosphates where it is found that the ratio is independent of chain length. The ratio of 0.5 for DETAPPA is close to the theoretically expected/empirical ratio by Masson of about 0.52. The ratio for the ion exchange method in U.S. Pat. Nos. 8,212,073 and 8,703,853 is much lower at approximately 0.33 to 0.375 pounds of DETA per pound of polyphosphoric acid. The new DETAPPA contains approximately an extra 43% of DETA ((0.5-0.35)*100/0.35), as compared to DETA in ion exchange method. The difference cannot be explained by the presence of sodium contamination.

The new method produces EAPPA with higher pH than the ion exchange method, an unexpected but highly desirable attribute of the new EAPPA compositions. The difference in pH of the two processes is indicative of fundamental difference in the two products as one contains sodium (U.S. Pat. Nos. 8,703,853, 8,212,073) and the new EAPPA does not. The new method has no waste stream, the handling and use of concentrated hydrochloric acid is eliminated, and eliminates sodium contamination in the EAPPA product.

Organic polymers have an inherent incompatibility with inorganic/organic polymeric compounds such as EAPPA limiting how much EAPPA can be added or is miscible. It has been found that special lubricants especially polyalpha olefins are necessary to enable good mixing at high loading. These lubricants also enable good draw for spinning of fiber. When a flame is applied to polymers containing EAPPA, these flame-retarded polymers often melt or deform which results in flaming. It is important to add drip suppressants or anti-drip agents such as fumed silica, a special grade of polytetrafluoroethylene (PFTE), and certain epoxy compounds to flame retarded compositions. The addition of lubricants for good processing is important in the formation of wire and cable jackets and fibers and glass reinforced engineering polymers. Epoxy containing compounds must still be added to polymeric compositions to stop formation of sticky surface in highly humid environments. Epoxy compounds also contribute to drip suppression via cross linking of neighboring chain. Lubricants contribute to drip suppression by enabling better dispersion of the inorganic flame retardant with the organic polymer. Thus, the roles of these ingredients are complex and intermixed.

Powdered forms of EAPPA and condensed EAPPA can be sprayed directly onto fires with a fire extinguisher instead of using mono-ammonium phosphate as the active ingredient. An aqueous solution of EAPPA can now be formed at a very broad range of concentrations, 10% and higher. The condensed EAPPA will be more effective than mono-ammonium phosphate as it is sticky, unlikely to drip, and self intumesces. The EAPPA either dry or aqueous, at concentrations 10% and higher possible for the first time, should be sprayed onto fuel in front of wildfire to stop the formation of embers, reduce rate at which fuel is consumed, reduce temperature of the fire all of which depress the heat flux emission. High molecular weight is more preferred as stickier. The higher level of EA in the EAPPA was found to result in increased intumescense, especially important in wildfires to separate flame and fuel by intumescent char layer.

For wildfires and other fires, it is preferred to use anhydrously prepared EAPPA that has been dissolved in water at room temperature. High molecular weight is more preferred as superior coating formed on the fuel. This is the first disclosure that EAPPA made with commercial PPA stops the formation of embers when coated onto wood, reduces rate of burn and surface temperature and thus low heat flux. That part of the wood that is wetted will not transform into an ember through which heat radiates, thus stopping the primary way, heat flux and embers, wildfires can be propagated so rapidly with wind. Previously, the property of ember elimination was only known for the syrup made by ion exchange that only occurs at one concentration. Now viscosity, concentration, and molecular weight are adjustable and concentrations of 75% are extremely effective. Variable concentration is important advantage as different fuels require different concentrations, as well as spraying equipment requirements. The char formed on flammable fuel remains intact despite the flame being applied for a long time. If the char had burned through, then the formation of an ember would be possible and a route for substantial heat to be radiated.

DETAILED DESCRIPTION OF INVENTION

The synthesis of flame-retardants using polyphosphoric acid is disclosed in U.S. Pat. Nos. 7,138,443, 8,212,073; WO 2011/049615 (PCT/US12/000247), PCT/US2003/017268, and U.S. Pat. No. 8,703,853. The entire disclosure is incorporated herein by reference. These references list the polymers both thermoplastic and thermoset that these flame-retardants are applicable to. Thus far, EAPPA is applicable in some form to all polymers. Application WO 2011/049615 (PCT/US12/000247) defines and lists the epoxy compounds that are applicable.

From these prior findings and the chemical literature, there would be little motivation to pursue the synthesis of ethyleneamine polyphosphates with commercial polyphosphoric acid (PPA), as low thermal stability would be expected. In prior work (US application 20060175587) with commercial PPA, ethyleneamine polyphosphates EAPPA were made by a process that resulted in a dilute aqueous solution, which was dried in a vacuum oven at a temperature of about 150° C. Heating an aqueous solution of polyphosphates at 150° C. causes rapid reduction in molecular weight especially at the pH used there.

The ion exchange method has deficiencies that the new method overcomes. In the ion exchange method, syrup containing water is dried under very high vacuum and high temperature to produce the ethyleneamine polyphosphate product. Syrup with a pH in the range of 4.5 to 5.5 was then dried in a vacuum oven to form EAPPA. This form of EAPPA from dried syrup was found to have a deterioration of pH. The pH was reduced to less than 4 and usually about 3.5. This pH lowering suggests that the vacuum drying of syrup results in degradation of the product. A pH of 3.5 is expected to cause degradation to polymers under extrusion as compared to a pH of 4.0 or higher. A low pH will also attract moisture, which is problematic for flame retarded polymers used in electrical applications.

The ion exchange (IX) process uses substantial amount of water and produces a substantial amount of waste product for disposal. The primary waste is dilute aqueous calcium chloride solution and dilute aqueous sodium chloride solution, both of which are contaminated with small amounts of phosphate, which complicates disposal to public sewer. Phosphorous is a controlled element and the waste sent to sewers must have a very low amount of phosphorous. The syrup from the ion exchange process was measured to contain 4260 mg/L, of sodium, which is substantial contamination. As a result, the product EAPPA from IX process will contain sodium (approximately 0.25 lbs per 55 lbs. of product), which will attract moisture and degrade electrical insulation properties. It is impossible for every sodium ion to be removed by the ion exchange process, as it is an equilibrium process during ion exchange resin regeneration. Finally, a large amount of concentrated hydrochloric acid is needed to regenerate the ion exchange column, which is undesirable for cost, safety, and environmental factors.

In this specification, it is shown that commercial polyphosphoric acid (PPA) can be reacted with ethyleneamines directly but requires a temperature whereby the EAPPA, EA, and PPA flows or that the EAPPA continually is broken up as the reaction proceeds and overcomes the reaction barrier. The reaction barrier to anhydrous direct formation was unanticipated and unknown until this work. The reaction barrier depends on grade of PPA and is small for a low molecular weight PPA and very high for a high molecular weight PPA. It had been assumed that these two liquids, for example, diethylenetriamine and polyphosphoric acid, would react to completion and there would be no reaction barrier to overcome. The reaction barrier was completely unexpected based on prior literature references[1,2,3,4] and this barrier is quite complex because of the polymeric nature of the product formed over a wide pH range and the lack of a solvent. The barrier is complicated by the EAPPA having a temperature at which it flows and mixes that is greater than that of PPA.

It was completely unexpected that an ethyleneamine polyphosphate formed with this new method using commercial polyphosphoric acid will have a different ratio of base to acid making its composition inherently different and resulting in new properties from that described in U.S. Pat. No. 7,138,443, US application 20060175587, and U.S. Pat. No. 8,212,073. It is also shown that the ethyleneamine polyphosphates with our new method based on commercial polyphosphoric acid can form syrup when dissolved in water contrary to the findings in U.S. Pat. No. 8,212,073. Masson (Energy & Fuels, Vol. 22, No. 4, 2008, pp. 2637-2640) states that "On an equal weight basis, the acidity of PPA in water is thus independent of chain length." In fact, the base acid ratio (EA/PPA) of the new EAPPA is now consistent with the theoretical expectation for reacting EA and PPA and consistent with the Masson findings. Masson results are empirical results for PPA with other organics and are referred to as theoretical. Finally, the new EAPPA can be transformed to high molecular weight by condensation, heating at high temperature under vacuum.

The primary means by which wildfires propagate rapidly is via windblown burning embers and heat flux. The wind blown heat flux preheats the fuel to be easily ignited by embers. It is difficult for an ember to ignite cold wood. According to fire fighters at Lake County Fire Department, Lake County, Calif., the heat flux can be so intense that 1) the PVC enclosure of vinyl windows melts and lets the heat in with embers and initiates burning in furnishings, and 2) the adhesive in roofing underlayment (sawdust plywood type products) and in siding (such as T1-11 plywood siding from Home Depot) decomposes to vapor and embers initiate combustion. In U.S. Pat. No. 8,703,853, it is indicated that sticks coated with syrup formed in the ion exchange process, according to U.S. Pat. No. 8,703,853, do not convert to burning embers when subjected to an intense flame. This syrup only forms at one concentration unlike the EAPPA formed here. It was suggested that syrup sprayed onto fuel in front of wildfire would stop the formation of embers and stop the wildfire. In U.S. Pat. Nos. 8,703,853 and 8,212,073, the necessity of stopping the heat generation was not recognized and not addressed. A deficiency of the currently used ammonium phosphate for wildfires is that it is not sticky, resulting in poor adherence to fuel, and does not self intumesce to form surface crust, all of which the EAPPA solution does.

Syrup formed in the ion exchange process deteriorates if stored a long time because it contains about 40% water and is acidic. The syrup can not be stored in metal cans because the aqueous EAPPA solution causes corrosion. Liquids are also subject to more scrutiny than solids when transported. Thus, it is needed to find a solid form of the syrup that could be sprayed onto fuel in front of fire or a way to make a liquid wildfire flame retardant that could be generated from a solid as the need for wildfire containment arose. For a liquid flame retardant to be effective, it is necessary that it stick onto the surface of fuel as a thin layer. Thus, the high molecular weight EAPPA has the right characteristics: can be dissolved into liquid form by adding water and has high molecular weight making it very sticky to anything it touches. The new form of EAPPA has a higher content of EA leading to more intumescent behavior, which is important in its uses as flame retardant for all uses.

Unless the context indicates otherwise, in the specifications and claims, the terms such as a flame retardant syrup, ethyleneamine polyphosphate, anhydrous ethyleneamine polyphosphate, flame retardant composition, filled flame retardant composition, flame retardant containing composition, polymer and flame retardant composition, filled flame retardant containing composition, ethyleneamine, polymer, and similar terms includes mixtures of such materials. Unless otherwise specified, all percentages are percentages by weight relative to total weight of composition and all temperatures are in degrees Centigrade (° C.) unless specified in ° F. For a given composition, percentages are by weight of final composition. All thermo graphic analysis (TGA) is performed in nitrogen at 20° C. per minute. The polymeric composition may include the flame retardant, other flame-retardants, and other ingredients as well as the resin. Ingredients such as drip suppressants, release agents, color, re-enforcement agents, heat stabilizers, lubricants, acid scavengers, etc. are routinely added and should be routinely applied. The term condensation and dehydration are used interchangeably as they refer to removal of water from EAPPA compositions to increase molecular weight and water that may have been added before or during the reaction. Adding water is not preferred.

Ethyleneamines are defined here as ethylene diamine and polymeric forms of ethylene diamine including piperazine and its analogues. A thorough review of ethyleneamines can be found in the Encyclopedia of Chemical Technology, Vol 8, pgs. 74-108. Ethyleneamines encompass a wide range of multifunctional, multi reactive compounds. The molecular structure can be linear, branched, cyclic, or combinations of these. Examples of commercial ethyleneamines are ethylenediamine (EDA), diethylenetriamine (DETA), piperazine (PIP), triethylenetetramine (TETA), tetraethylenepentamine (TEPA), and pentaethylenehexamine (PEHA). Other ethyleneamine compounds which are part of the general term ethyleneamine (EA) which may be applicable are, aminoethylenepiperazine (EAP), 1,2-propylenediamine, 1,3-diaminopropane, iminobispropylamine, N-(2-aminoethyl)-1,3-propylenediamine, N, N'-bis-(3-aminopropyl)-ethylenediamine, dimethyl aminopropylamine, and triethylenediamine. Ethyleneamine polyphosphate can be formed with any of these ethyleneamines.

Polyphosphoric acid (PPA) is an oligomer of H3PO4. High purity PPA is produced either from the dehydration of H3PO4 at high temperatures or by heating P2O5 dispersed in H3PO4. The equilibrium for these reactions produces different chains lengths and distributions. The dehydration method tends to produce short chains, whereas the dispersion method usually produces chains with more than 10 repeat units, which are more preferable in making the compositions of this invention. Many different temperatures are used in the reaction of P2O5 and 85% concentration phosphoric acid in making PPA.

PPA is available in various grades, the naming of which can be confusing as the percentage can exceed 100%. One hundred percent phosphoric acid contains 72.4% P2O5 as calculated from the formula weight ratio P2O5/H3PO4. Similarly, Pyrophosphoric acid (H4P2O7) contains 79.8% P2O5 as calculated from the ratio P2O5/H4P2O7. The ratio of these P2O5 contents provides a relative phosphoric acid Content, which for pyrophosphoric acid is 79.8%/72.4%=110%. Due to high viscosity, PPA is difficult to pour and stir at room temperature, but is much easier to work with at temperatures above 60° C.

The production of PPA provides a distribution of chain lengths, where the number of repeat units in the PPA chain n, varies from one chain to the next. The 105% PA grade from Innophos Corp. contains for the most part short monomeric and dimeric segments, ortho (54%), pyrophosphoric (41%) and 5% triphosphoric and pours easily and would not be expected to provide a route to high molecular weight EAPPA. In the higher 115% grade, little monomer is left as most of the chain lengths are 2-14 units long. This increase in chain length leads to chain entanglements and explains the increased viscosity of the higher grades. Only the 117% grade (3% Ortho, 9% pyro, 10% tri, 11% tetra, 67% higher acids), 115% grade (5% ortho, 16% pyro, 17% tri, 16% tetra, 46% higher) and 105% grade are used throughout the examples. They are from Innophos, Trenton, N.J. All grades of PPA are claimed regardless of how formed. Sodium content of such PPA is incidental and very low and considered sodium free for our purposes.

Properties of PPA's have been known. Shen[4] has measured the distribution of various grades of PPA with results similar to Innophos. It was stated in U.S. Pat. Nos. 7,138,443 and 8,212,073 that the orthophosphoric content of commercial polyphosphoric acid would be to high for the EAPPA to perform as well as that formed by IX process and which should not contain any orthophosphoric.

The versatility and general utility of PPA arise from the fact that it is a mild reagent even though it is a strong dehydrating agent. Generally, it does not bring about charring of organic compounds. The boiling point of PPA 117% at 1 atmosphere is 550° C. It is also possible to form the EAPPA by combining and reacting orthophosphoric acid and P2O5 in a kettle and then adding EA all in the same kettle to synthesize EAPPA directly, but not preferred.

Polyphosphoric acid will decompose to lower molecular weight material rapidly if dissolved in water, especially at elevated temperature. The key to success in this contribution is a result of forming ethyleneamine polyphosphates without the use of water or sodium contamination and solvent free. Water could be added but needs removal in the final drying step if destined for plastics.

Long chain sodium polyphosphates were used with the ion exchange process in U.S. Pat. Nos. 7,138,443, 8,212,073; 8,703,853, and WO 2011/049615 (PCT/U512/000247). The character of PPA by two different processes (dehydration and dispersion) is not the same and PPA made from sodium polyphosphate in the IX process is also different.

FDA has a boiling point of 117° C. Piperazine has a boiling point of 146° C. TETA has boiling point of 266° C. and DETA is 207° C. The dielectric constants for EA: DETA (=12), for EDA (=13.3) for TETA (=10.24) and for TEPA (=9.93). Masson (Energy & Fuels, Vol. 22, No. 4, 2008, pp. 2637-2640) states that PPA dos not readily forms ions and react with an organic compound if the dielectric constant is less than 15, as are all the EA compounds. "On a weight basis, however, the acidity of PPA is equal to that of H3PO4, which also releases one proton per phosphorus atom. Moreover, upon dissolution of PPA in water, the equilibrium shown so that PPA reverts back to H3PO4. On an equal weight basis, the acidity of PPA in water is thus independent of chain length." The molecular weights are: H3PO4 98, PPA (HPO3)$_n$ 80, EDA 60, DETA 103, piperazine 86.1, TETA 150, and TEPA 189.3. The EA used in this contribution have dielectric constant less than 15 and thus there may be little ion formation when EA and PPA are reacted and thus the large endothermic reaction is unexpected. The estimated or theoretical or empirical reaction ratios based on Masson, H3PO4 molecular weight, and ionicity at which EA reacts with PPA are: EDA 0.61 (60/98), piperazine 0.88 (86.1/98), DETA 0.52 (103/2*98), TETA 0.51 (150/3*98), and TEPA 0.48 (189.3/(4*98). It is preferred to have an ionicity near 4.0, to make it less likely that EA molecules could condense to release ammonia molecule. Empirically, the ratio was found to be near 0.5 for DETAPPA and TETAPPA to obtain an EAPPA with final pH near 4.0. If the molecular weight of PPA 80 were used, then the ratio for DETA would be 0.57 (103/2*80) substantially different from experiment. (Masson states "For PPA to dissociate into PPA− and H+, the medium must be of sufficiently high dielectric constant (ε). Water is very polar. It has the highest dielectric constant of all solvents, ((HPO3)$_n$=80), closely followed by H3PO4." Based on this, the EA's do not form ions with PPA. This plausible theory does not necessary hold for all EA's and does not limit this invention. The estimates are based on H3PO4 not PPA and is considered empirical. It would be impossible to predict exactly at what temperature and ratio anhydrously ethyleneamines will react with PPA to form EAPPA[1,2,3] as these compounds form over wide pH range.

It is not surprising the ion exchange approach gave results that are different due to water presence, sodium contamination, high temperature drying of wet product, and different inherent polyphosphate molecular weights as compared to anhydrous approach detailed in this specification. Ion exchange leaves some sodium on the IX resin that will contaminate the product and change ratio of acid to base.

In PCT/US12/000247, it was emphasized in great detail that commercial polyphosphoric acid as practiced in these works was unsatisfactory as compared to the use of polyphosphoric acid prepared by ion exchange as described in U.S. Pat. Nos. 7,138,443, 8,212,073, 8,703,853, and WO 2011/049615. It was specifically stated that it was preferred to use polyphosphoric acid prepared by ion exchange. Throughout this prior work, it is stated often that ethyleneamine polyphosphates made with commercial polyphosphoric acid do not form syrup when dissolved in water with formation of syrup only occurring with ion exchange. It is further stated in these prior works that formation of syrup is indicative of high molecular weight ethyleneamine polyphosphates. The prior IX work did not appreciate the sodium contamination and its negative impact on those compositions.

The ratio approximately is 0.33 to 0.375 pounds of DETA per pound of polyphosphoric acid for the ion exchange method. Sodium polyphosphate is approximately 20% sodium and 80% polyphosphate leading to the conclusion of 0.33 to 0.375 lbs. per lb. polyphosphate content. The example in U.S. Pat. No. 8,212,073 uses 6170 g (13.6 lbs.) DETA for 50 lbs. of sodium polyphosphate (40 lbs. PPA after sodium removal), which is 0.34 lbs. DETA per lb. polyphosphoric acid. The method presented here is at a ratio of 20 lbs. DETA per 40 lbs. PPA. This sample of DETAPPA made with ion exchange contains sodium contamination of about 0.25 lbs./55 lb. product.

DETAPPA has been made directly with commercial PPA grades 105, 115, 117 and DETA nearly at the theoretical base to acid ratio. We have already indicated the necessity of condensation to higher molecular weight to obtain a product usable in polymer extrusion applications.

Reaction barrier can be thought of as the height of the potential barrier (sometimes called the energy barrier) separating two minima of potential energy (of the reactants and product of a reaction). For a chemical reaction to proceed at a reasonable rate, there should exist an appreciable number of molecules with energy equal to or greater than the reaction barrier. Good mixing requires all ingredients (EA, PPA, EAPPA) in the reaction including the EAPPA product to flow well. For practical reasons, the reaction should proceed at a rate that makes commercial production cost effective and viable. A lower temperature would require a longer time. As EAPPA is a polymer, the reaction energy or reaction barrier is the temperature at which the reactants EA and PPA including EAPPA mix well to completion. Otherwise, the reaction of EA and PPA will stall at a low pH such as 2 before the reaction of EA and EAPPA has completed to a value between 4 and 6 as desired, which was not anticipated.

For DETAPPA, the reaction requires an approximate ratio of two parts of PPA by weight to one part DETA by weight. The reaction of DETA and PPA is considered incomplete if the reaction stops at a lower pH and not all the EA is consumed. PPA 105% and PPA 115% flow at room temperature. The solvent free reaction of DETA with PPA is complicated in that DETAPPA formed with any of these acids is a solid at room temperature. The higher the molecular weight, the higher the temperature at which these compounds flow. One has to build into the experiment that the mixing of EA and PPA is difficult. If the temperature in the reaction vessel is too low, then EA, PPA, and EAPPA do not mix adequately. The EAPPA formed at the interface will harden and the reaction will not complete. Product will be formed but the pH will be near 2.0, pH will not be uniform, and a pool of EA and PPA remains. The temperature at which a complete reaction occurs is lowest for PPA 105%. If the temperature of the reaction vessel is 200° C. then the reactions will probably complete for all the molecular weight grades of PPA. The difficulty is that raising the temperature of PPA 117% or PPA 115% to 200° C. before introducing EA will result in corrosion problems. There is no apparent corrosion problem for EAPPA being processed at a temperature of 200° C. The corrosion problem is further minimized if the reaction is completed in minutes. Thus, introducing both EA and PPA initially at low temperature solves corrosion problems. The EA and PPA can be added simultaneously so that the product is continuously formed.

The difficulty in getting complete reaction of EA and PPA of any grade is overcome by adding the ingredients in a closed high intensity mixer that pulverizes the EAPPA as formed so that the EA, PPA, and EAPPA can go to complete reaction and obtain the desired pH. A relief/condensation mechanism valve might be necessary if free volume of reactor is too low. It was completely unanticipated that DETAPPA formed with PPA 115% very low pH can form a solid at that temperature and stop the reaction unless the EAPPA product is continually broken up or pulverized. It may also be necessary for heating to be added to the reaction vessel as the EAPPA has to melt to enable full reaction. The experiments reported here had so much heat generated that no heat needed to be added with the self generated final temperature being about 200° C., but only if EAPPA was broken up or pulverized as the reaction progresses. The reaction is so quick that unwanted side reactions were not observed such as cross linking of EA molecules, even in a closed container. Thus, it was fortunate that unwanted reactions did not occur in the closed container, although some steam was allowed to escape as the reaction container is not sealed.

It previous work in U.S. Pat. No. 8,212,073 and US application 20060175587, the reaction vessel was open and the amounts of ingredients were very low. Efforts at reacting EA and PPA directly was abandoned as these corrosive materials were escaping, an unsafe situation and reliable product could not be accumulated. If enough water is added to PPA or EA, the reaction is slowed and the heat dissipates in the water. But an inferior product with lower molecular weight results as is established in U.S. Pat. No. 8,212,073 and US application 20060175587.

The preferred PPA is from grade PPA105% to PPA 117% reacted with EA at room temperature initially. The more preferred is grade PPA 115%. The preferred method is to combine the ingredients together in a high intensity mixer at room temperature or even 0° C. and mix fast enough so that a solid does not form. The exothermic heat is so intense that the EAPPA temperature was found to be raised to near 200° C. within five minutes, even if the reaction had been started at 0° C. If the reaction volume is too small, EA could be added slowly to the PPA or added together slowly so that the risk of over heating/pressure the vessel does not occur or vice versa. The EAPPA product, before can then be subjected to condensation by any method such as: vacuum heating at 200° C. or higher to raise molecular weight and greatly reduce ortho and pyrophosphate content. For EAPPA made with PPA 105%, the weight loss during condensation/molecular weight enhancement will be about 6% and result in a product that forms about 3 ml syrup when 3 g are dissolved in 10 ml water. For some applications such as firefighting, it may not be necessary to condense to higher molecular weight. The as is product before condensation did not form syrup for EAPPA made with PPA 105%. The molecular weight enhancement was found to leave the pH unchanged, an indication that the new process does not deteriorate product as had the ion exchange drying process, probably as no water involved and no obvious degradation pathways.

If a high intensity mixer is unavailable, an alternative procedure for EA and PPA 117% or PPA 115% is to add PPA to EA at high temperature. The method for reacting DETA, boiling point 207° C., with PPA 117% was to drip the heated PPA acid unto DETA and then stir until complete conversion. DETA was heated to a temperature near its boiling point, 200° C. to make the reaction proceed at a reasonable rate. The rate of addition of PPA cannot be too fast as it is exothermic. Such a high temperature for the good mixing of EA and PPA appeared to be necessary to overcome the high viscosity of PPA 117% and the resultant DETAPPA that also has very high viscosity. This product formed syrup when dissolved in water, a distinct difference from the expectations of prior work as referenced. However, this DETAPPA behaved poorly when added to nylon 66 in an extruder unless this DETAPPA had been subjected to condensation.

The identical procedure was followed at a temperature of 160° C. but did not yield a product that melted into the polymers in a Brabender and did not yield syrup when dissolved in water. However, if the time of reaction had been extended it would be expected that the reaction might have gone to completion as it is exothermic. For certain the temperature of 160° C. does not overcome the viscosity of PPA 117C and DETAPPA 117% as does a temperature of 200° C. and proper mixing was an issue. Taking a long time for reaction is not as practical as compared to using a higher temperature. The risk of unwanted side reaction will occur as the temperature is raised or time is increased. There is inherently corrosion concerns with handling PPA 117% at temperatures above 160° C. and technical expert at Innophos recommends avoiding if possible. Condensation of EAPPA for all grades to high molecular weight occurs very slowly if at all in vacuum oven set at 150° C.

From an economic standpoint, it is preferred to use a grade of PPA between 105% and 115% to form EAPPA and then condense by some method to form higher molecular weight.

A person knowledgeable in this chemistry could easily optimize the temperature conditions with the available equipment and the order of reaction of PPA with DETA, EDA, piperazine, TETA and other ethyleneamines. Mixing the ingredients together in a stainless steel heated mixed vessel, like a high intensity mixer, without catalyst may be the cost effective approach.

It is preferred that the flame retardant melts and can be extruded into polymers such as PP, PE, EVA, TPU, and nylon 66. Thus, reaction conditions and vacuum drying conditions need to be chosen that the resultant product has such attributes. It is preferred to subject all compositions to condensation to reduce the potential of problems when extruding EAPPA into polymers. Condensed EAPPA has been found thus far applicable to all thermoplastics and thermosets.

All grades of PPA will contain some contamination of orthophosphoric and pyrophosphoric acid, which will result in some low molecular weight EAPPA that is undesirable for best performance. One method of condensation is vacuum heat treatment of EAPPA to decrease the amount of these low molecular weight forms of EAPPA. Initially, the vacuum pressure changes rapidly but then stabilizes. The preferred conditions such as temperature and length of time depend on factors such as size of vacuum pump, temperature and size of oven, amount of material being condensed, surface area exposed, thickness, and amount of mixing if any. The preferred conditions are indicated for a sample size of 500 g in two pans in vacuum oven cavity size 9 in×9 in×9 in and a vacuum pump that can reach a pressure of 5 TORR when the vacuum oven is empty. The required conditions could change for a rotary vacuum oven with a large batch or with another condensation technique or method. The preferred conditions for molecular weight enhancement are a final vacuum less than 45 Torr maintained for at least 20 minutes and a temperature of at least 180° C. The more preferred is a vacuum less than 30 Torr maintained for at least 20 minutes and a temperature of at least 200° C. The most preferred is a vacuum less than 15 Torr maintained for at least 20 minutes and a temperature of at least 220° C. It may be necessary to raise the temperature by 20° C. to 50° C. at termination of molecular weight enhancement to be able to extract the product. The initial starting vacuum is lower initially as water is rapidly extracted out.

Other condensation techniques that result in increased molecular weight for condensation polymers should be of value, such as hot nitrogen applied to small pellets for a period of time or thin film dehydration at high temperature. We thus claim condensation by any technique that extracts moisture from the composition to raise molecular weight and causes the EAPPA to equilibrate to a higher average molecular weight.

The preferred ethyleneamines are EDA, DETA, TETA, PETA, and piperazine. The most preferred are DETA, TETA, and piperazine. EAPPA's are made with an EA/PPA ratio chosen so that the pH of a 10% aqueous solution by weight of the composition is in the range 2 to 7.5. The preferred is pH 3.5 to 6.5. The more preferred is pH 3.5 to 5. The most preferred is pH 3.75 to 4.5. Alternatively, the less preferred method to describe the reaction ratio of EA to PPA is by weight of composition between 0.55 and 0.61 for EDA, between 0.82 and 0.88 for piperazine, between 0.46 and 0.52 for DETA, between 0.45 and 0.51 for TETA, and between 0.42 and 0.48 for PETA. This formula has only been tested for DETAPPA and TETAPPA, thus making the compositions described by pH more reliable.

Three types of DETAPPA have been described: 1) DETAPPA formed by reaction of DETA and commercial PPA and water and which has serious shortcomings as detailed in U.S. Pat. Nos. 7,138,443 and 8,212,073, 2) DETAPPA formed from DETA and polyphosphoric acid formed by ion exchange which is contaminated with about 0.4% sodium and formed at a non theoretical ratio near 0.35, and 3) DETAPPA formed anhydrous from DETA and commercial PPA and which can be condensed by any method to higher molecular weight and which has the best properties as detailed here.

Form 1) has inherently lower molecular weight du to water and heat. Thus, it is preferred to form product as in form 3) without water as less cost and significant quality improvement. Form 2) via ion exchange has issues with waste stream, sodium contamination and pH as it is made in an aqueous state and dried from an aqueous state. If types 2) and 3) are dissolved in water at 3 g per 10 g water, the interface between the two phases disappears with time. Type 3) is stable for the longest time indicating higher molecular. A big advantage of 3) is that aqueous solutions can be formed at wide range of concentrations even 75%. The syrup of 2) forms at one concentration. Similar behavior is expected for EAPPA's made with EDA, TETA, piperazine, and TEPA.

The ethyleneamine polyphosphates of this invention melt into polymers. The melt flow of the polymers is similar to that of the pure polymers, whereas particulate flame retardants tend to be drip suppressants by decreasing melt flow substantially. When EAPPA flame retarded polymers are subjected to a flame they will soften and sag or drip. To overcome the softening, an anti-drip agent is useful. Fumed silica both hydroscopic and hydrophobic fumed silica are quite useful and are very well defined in U.S. Pat. No. 8,703,853 and PCT/US12/000247. The preferred fumed silica is Aerosil R972 by Evonik Corporation. Another widely used anti-drip agent is fine particle PFTE 6C made by DuPont Co, Wilmington, Del. Epoxy containing compounds cross link with EA. The epoxy tends to serve as drip suppressant polymers.

It is useful to add a lubricant for some compositions, especially those with high concentration of additives. The preferred lubricant is polyalpha olefin from Chevron such as Synfluid 150. Polyalpha olefins are 100% synthetic chemical compound. Specific type of olefin (organic) that is used as a base stock in some synthetic lubricants. Poly-alpha-olefin (or poly-α-olefin, abbreviated as PAO), is a polymer made by polymerizing an alpha-olefin. It is a specific type of olefin (organic) that is used as a base stock in the production of some synthetic lubricants. An alpha-olefin (or α-olefin) is an alkene where the carbon-carbon double bond starts at the α-carbon atom, i.e. the double bond is between the #1 and #2 carbons in the molecule. The lubricant can be melted into the EAPPA. As EAPPA is ground to a particulate, the lubricant can be added to the particulate EAPPA. Other ingredients such as plasticizers, UV stabilizers, color, and glass reinforcement can be added to enable particular characteristics.

The definition of epoxy and applicable epoxy compounds are found in PCT/US12/000247. The ethyleneamine polyphosphates are applicable to all polymers thermoplastic and thermoset and a list is found in PCT/US12/000247.

Basically, the EAPPA of this invention for polymer extrusion must be made with a method such that it melts into widely used polymers such as PE, PP, EVA, TPU and nylon 66 at a concentration of at least 15% by weight. These polymers are representative of broad spectrum of polymers that are applicable and the polymer grade is chosen to have a melt flow that accepts fillers. EAPPA melts into polymer grafting agent such as Elvaloy PTW made by Dupont Co. and epoxies such as Epon SU8, Epon 828, EPON 1007F, and EPON 1009F made by Momentive. The preferred epoxy compounds are Elvaloy PTW, Epon SU8, Epon 828, EPON 1007F, and EPON 1009F.

The goal is to create thermoplastic compositions at high loadings of flame-retardants to achieve very high flame retardant (FR) performance. Most of the examples will contain approximately 67% FR loading. The polymers do not readily accept a 67% loading of our polyphosphate FR that melts into the polymer, so a particulate FR has been added. The particulate is FP2100J (ADI STAB FP2100J from Adeka corp.). It is possible that at lower loading of FR a different epoxy containing compound may be chosen. At a 67% loading, the preferred epoxies will be chosen from the group consisting of Elvaloy PTW from Dupont Company, Epon SU8, Epon 828, Epon 1009F and Epon 1007F. The preferred polymer is EVA Elvax 260 with VA content 28% from DuPont Co. This composition can be cross linked if high temperature performance required. It is preferred that other phosphorous or nitrogen containing particulate flame retardants be part of the final composition. For example, melamine, melamine polyphosphate, Melapur 200 from BASF, Zuran 9 from China, Prenifor from China, APP (ammonium polyphosphate made by several companies), metal phosphinates from Clariant Corporation, melamine cyanurate, ethyleneamine phosphates, and ethyleneamine pyrophosphates. The preferred is FP2100J by Adeka.

For a high loading of FR. near 50% to 67%, the preferred amount of EAPPA is 22% to 57% by weight and 12% to 40% by weight of phosphorous flame retardant. It is also preferred to add a drip suppressant such fumed silica at a loading of at least 0.25% and the preferred is Aerosil 8972. The preferred phosphorous flame retardant is FP2100J by Adeka Corp. To prevent stickiness in a high humidity environment, it is important to add an epoxy compound. The preferred epoxy compound is Elvaloy PTW at a loading of at least 0.3%, A lubricant is also preferred at a loading of at least 0.2% to yield good melt strength. The preferred lubricant is a polyalpha olefin such as Synfluid 150 by Chevron Phillips, Houston, Tex. A 67% FR loaded sample should pass plenum cable test UL910 halogen free.

Another aspect of this invention is to mill EAPPA into very fine particles, which can be added to thermoset polymers before cure or to thermoplastic polymers. It is also possible to melt EAPPA into thermoset epoxies that are solids at room temperature. It is likely that with the right process, EAPPA can be added to all epoxies, including epoxies that are not solid at room temperature.

It is claimed in this specification that the EAPPA and polymer compositions containing EAPPA may need to contain an epoxy containing compound. The epoxy containing compound reacts with EAPPA to stop certain flame retarded polymeric compositions from becoming sticky when subjected to moisture from air. The problem usually occurs at high loadings and high humidity conditions. The applicable epoxy containing compounds are detailed in PCT/US12/000247.

The epoxy compound can be melted into the EAPPA, although for liquid epoxy compounds can be difficult. As EAPPA is ground to a particulate, the epoxy compound can be added to the particulate EAPPA, especially for liquid epoxy compounds. This is a preferred method to add epoxy compounds to form flame retardant containing compositions, especially if the epoxy compound is a liquid.

An ember is usually formed when a fire has only partially burned a piece of fuel, and there is still usable chemical energy in that piece of fuel. Often this happens because the usable chemical energy is so deep into the center that air (specifically oxygen) does not reach it. It continues to stay hot and does not lose its thermal energy quickly because combustion is still happening at a low level. The small yellow, orange and red lights often seen among the embers are actually combustion and radiating heat. There just is not enough combustion happening at one time to create a flame.

If a lignocellulosic, such as a 0.25 inch wooden dowel, is coated with an aqueous solution about 1 mil thick of EAPPA and subjected to a propane torch, a thin crust forms on the surface that protects the interior. Such behavior had only been reported previously for syrup formed by ion exchange. The propane torch is so hot that the char may have a slight glow, which quickly disappears when the torch is withdrawn. The char quickly returns to room temperature whereas an ember stays hot a long time. If torch is applied a long time, the interior will eventually turn to char thereby reducing the fuel load. The crust was found to protect the dowel from forming burning embers and reduce the fuel load as most of the dowel is not consumed by the fire. Even if a coated fuel is heated for an extended period of time so that only char remains, no ember ever formed which was not discovered in U.S. Pat. No. 8,212,073. The dowel does burn with a very small flame but goes out quickly once the torch is removed, which thereby slows the burn rate. It was expected that the flame from the torch would burn through the char and an ember would form over time. Instead the char resisted "burn-through" and the fuel below the char slowly escaped and the dowel becomes hollow inside. The hollow formation was unexpected. By stopping burning embers, reducing fuel load and fuel consumption rate, the progression of forest fires can be stopped as heat is now radiated over a long time and slow rate. The high heat flux is no longer occurring for coated fuel. To stop a forest fire, simply spray a thin coating of EAPPA solution onto the fuel in front of a forest fire. It is preferred that the coating be at least 0.25 mil thick and coat at least 25% of the fuel. Coating at least 50% of the fuel is preferred. A coating thickness of at least 0.5 mil is more preferred and a thickness of 1.0 is most preferred. The EAPPA solution should have a ratio of EAPPA to water of at least 30/70, depending on the fuel. For wildfire control, more preferred is 40/60. Most preferred is at least 50/50. This is the first time that it is recognized that EAPPA made with commercial PPA stops the formation of embers, lower burn rate, and surface temperature all of which curtail the high heat flux. Stopping ember formation and excessive heat flux is a more meaningful requirement than formation protective barriers as discussed in U.S. Pat. No. 8,212,073. The char or surface crust separates fuel from fuel greatly reducing vapor formation.

EAPPA solution made with high molecular weight PPA is preferred for fighting fires, especially wildfires. High molecular weight is very sticky. Sprayed high molecular weight droplets onto fuel will adhere to the surface and spread into film if the temperature is high enough. The condensed EAPPA is more preferred but costs the most and takes longer to dissolve into water. This method of fighting fires is preferred as EAPPA in solid form is shipped to wherever it will be used. As the need for stopping a fire occurs, then water is added to dissolve solid EAPPA and can then be applied to the fire. Thus, the method consists of first forming solution at desired concentration and then applying to a fire. This technology enables a 75% solution with even high molecular weight that still sprays. The high concentration solutions would be preferred for other types of fires such as oil, chemical, and tires where the fire is sprayed directly as the fire is contained and burning from underneath. Such fires must be cooled and air starved as the only option. EAPPA is unlikely to become part of a chemical reaction that adds to conbustion.

A solution of EAPPA formed by adding together water, EA, and PPA in the synthesis becomes very hot during the synthesis. The water and acidity create molecular weight reduction path to inherently lower molecular weight. This aqueous EAPPA form not preferred as much less sticky than the anhydrous which does not contain a water degradation pathway. No syrup formed in such synthesis indicating lower molecular weight. This form is still effective, but not preferred. This form further degrades to lower molecular weight with time, which was very obvious from the viscosity of a one year old sample, which was low.

EXAMPLES

Example 1: Diethylene triamine (DETA) and PPA 117C are reacted at a temperature of 200° C., very near the boiling point of DETA. Heated polyphosphoric is added slowly over a period of 60 minutes until the desired pH, one part by weight DETA and two parts by weight PPA. Polyphosphoric acid 117C from Innophos is chosen as it has the highest molecular weight. The reaction is heated to ensure the reaction is completed and then cooled. The product is then broken up. The pH was 4.0. TGA performed at 20° C. per minute in nitrogen showed a wt. loss of 1% at 308° C. A higher thermal stability could be obtained by subjecting the DETAPPA composition to condensation. The composition forms syrup when dissolved in water, which was unexpected.

Example 2: Diethylene triamine (DETA) and PPA 117C are reacted at a temperature of 160° C., much lower than the boiling point of DETA, as in example 1. Polyphosphoric is added slowly over a period of 60 minutes. Polyphosphoric acid 117C from Innophos is chosen as it has the highest molecular weight. The reaction is heated for a few hours as in example 1 and then cooled. The product is then broken up. The pH is approximately 4.0. The product is not brittle and can be pulled apart by hand. The product is also streaked indicating that the product is not uniform in composition, a result of inadequate mixing.

Example 1—Syrup: Dissolve 3 g of example 1 in 10 ml of water. At least 1.5 ml of syrup precipitates to bottom of solution. Syrup is a viscous liquid that settles to the bottom of the reaction vessel and that a clear line of distinction is formed. When the solution is stirred, a cloudy solution is formed. The pH is approximately 4.0. It was unexpected that the amount of syrup exceeded the amount expected for good performance in U.S. Pat. No. 8,703,853 without subjecting the EAPPA to condensation.

Example 2—No Syrup: Dissolve 3 g of example 2 in 10 ml of water. No distinct syrup forms at bottom of solution. There is a distinct color change at the bottom of vessel but it could not be collected as no clear line of distinction. When the solution is stirred, it does not become cloudy, which should indicate low molecular weight and fundamentally different from Example 1.

Example 1253: To a Brabender is added a composition consisting of 28 g of example 1, 14 g of FP2100J from Adeka corporation, 16 g of Elvax 260 from the DuPont Company, and 5 g of Elvaloy PTW from the DuPont Company. The mixing temperature is 173° C. The sample is mixed for 4 minutes and then extracted. Plaques of 1/32 inch thickness were formed. The plaques are flexible and do not crease when bent. Samples pass UL94 V0 at 1/16 inch.

When this same composition using Example 1 was run on a twin screw, the strands had poor properties. Thus, the PNS of example 1 was subjected to condensation, vacuum drying at 250C for 60 minutes. The same composition as in Example 1253 now performed very well. The strands were very good and the composition was used to prepare a plenum cable.

Comparative Example 523: To a Brabender is added a composition consisting of 28 g of DETAPPA from comparative example 1 of U.S. Pat. No. 8,703,853 14 g of FP2100J from Adeka Corporation, 16 g of Elvax 260 from the DuPont Company, and 5 g of Elvaloy PTW from the DuPont Company. The mixing temperature is 173° C. The sample is mixed for 4 minutes and then extracted. Plaques of 1/32 inch thickness formed. The plaques are not as flexible as Example 1253 and crease when bent. Samples pass UL94 V0 at 1/16 inch.

Example Bad Mix: To a Brabender is added a composition consisting of 28 g of example 2, 14 g of FP2100J from Adeka corporation, 15 g of Elvax 260 from the DuPont Company, and 6 g of Elvaloy PTW from the DuPont Company. The mixing temperature is 173° C. The sample is mixed for 4 minutes. The sample did not mix. The flame retardant of example 2 does not mix into the polymer as did the flame retardant of example 1. There is a fundamental difference between DETAPPA of examples 1 and 2.

Example 1255: To a Brabender is added a composition consisting of 28 g of example 1, 14 g of FP2100J from Adeka corporation, 15 g of Elvax 260 from the DuPont Company, and 6 g of Elvaloy PTW from the DuPont Company. The mixing temperature is 173° C. The sample is mixed for 4 minutes. The sample did mix. The plaques are flexible and do not crease when bent. Samples pass UL94 V0 at 1/16 inch.

Example 1254: To a Brabender is added a composition consisting of 28 g of example 1, 14 g of FP2100J from Adeka corporation, and 21 g of Elvax 260 from the DuPont Company. The mixing temperature is 173° C. The sample is mixed for 4 minutes and then extracted. Plaques of 1/32 inch thickness formed. The plaques are not very flexible and crease when bent. This indicates that Elvaloy PTW is important for getting a good dispersion of the composition ingredients. Samples pass UL94 V0 at 1/16 inch.

Example 1252: To a Brabender is added a composition consisting of 28 g of example 1, 14 g of FP2100J from Adeka corporation, 15 g of Elvax 260 from the DuPont Company, 1 g of Epon Su8 from Momentive Corporation, and 5 g of Elvaloy PTW from the DuPont Company. The mixing temperature is 173° C. The sample is mixed for 4 minutes and then extracted. Plaques of 1/32 inch thickness formed. The plaques are not flexible and do crease when bent indicating that inclusion of SU8 not recommended for this composition. The Epon Su8 might work at a lower loading of the flame retardant of example 1. Samples pass UL94 V0 at 1/16 inch.

Example 1256: To a Brabender is added a composition consisting of 18 g of example 1, 6 g of FP2100J from Adeka corporation, 28.5 g of Laripur 9060 from COIM Corporation Milano, Italy, 2.4 g Elastollan C85a from BASF Corporation, and 5.5 g of Elvaloy PTW from the DuPont Company. The mixing temperature is 190° C. The sample is mixed for 4 minutes and then extracted. Plaques of 1/32 inch thickness formed. The plaques are very flexible and do not crease when bent. Samples pass UL94 V0 at 1/16 inch.

Example Sodium Content: 300 ml diethylenetriamine polyphosphate syrup from U.S. Pat. No. 8,212,073 made by ion exchange method was analyzed for sodium content. The sodium concentration in the syrup was 4260 mg/L. Such a sodium concentration in the syrup would result in a contamination of 0.25 lbs. of final product.

Example 188: 27 g of TPU from Bayer corporation, 5.5 g Elvaloy PTW, 6 g of FP2100J, 3.5 g of TPU Elastollan C85a, 1.2 g Aerosol R972, 1.2 g Epon SU8, and 18 g of Example 1 were mixed in a Brabender for 4 minutes at 190° C. The sample exhibited very good flexibility and strength and passed UL94 V0 at 1/16".

Example 182: 11.2 g of Example 1, 5.6 g FP2100J, 35.2 g PP from GE Chaplin, 4 g Elvaloy PTW were mixed in a Brabender for 4 minutes at 190° C. The samples had good apparent good mechanical properties.

Example 186: 12. g of Example 1, 6 g FP2100J, 23 g PP from GE Chaplin, 4 g Elvaloy PTW and 15 g chopped glass were mixed in a Brabender for 4 minutes at 190° C. The samples had good apparent good mechanical properties.

The FR of this invention is a polymer. Thus, heating under vacuum was found to produce a higher molecular weight for the anhydrous flame retardant composition. The higher molecular weight will also result in a higher thermal stability. For condensation polymers, it is well known that heating under vacuum at a temperature near the melt temperature leads to higher molecular weight. Examples of such condensation polymers would be nylon and polyester. In a Brabender where samples are not subjected to high shear, the EAPPA made without condensation are adequate. It will be found, that samples run on a twin screw with substantial shear, should be made with EAPPA that has been subjected to condensation and contains minimal amount of low molecular weight EAPPA.

The next experiments demonstrate the preferred PPA. The equipment consists of 1) a 4 L pressure cooker that traps the exothermic heat with the lid having a hole for the mixing element, 2) a four prong mixing element normally used for mixing paint powered by a belt driven drill press set at 3600 RPM, and 3) a hot plate. This equipment does not have the capability to break up EAPPA that might form a solid as the reaction progresses. The equipment had to be stopped so that the solid could be broken up manually.

Experiment 105: 180 g of DETA and 360 g of PPA 105% were added to the pressure cooker. The pressure cooker and hot plate were at a temperature of 0° C., as the experiment was performed in freezing room with no heat. The hot plate setting is such that the temperature of the hot plate will reach a temperature of 170° C. but will take about 30 minutes for the hotplate to reach that temperature. The mixing and the hot plate are started simultaneously. The EA and PPA 105% start reacting after about 2 minutes as some steam begins to leak out. The hot plate was still cold. After about 5 minutes the reaction appeared complete and the pot was very hot from the exothermic heat. At 10 minutes, the reaction was stopped. A temperature probe placed between the pot and the hot plate had a reading of 195° C. The product was very viscous but the drill press could stir the DETAPPA product. The yield of product was 532 g indicating a 100% yield as expected. The pH of the product was approximately 4. to the accuracy of pH paper. No syrup formed when dissolved in water. It was unexpected that the reaction completed without there being a devise to wipe off the sides of the reactor during mixing, a result of very high boiling points the probable reason. Another factor is high surface tension and high molecular weight of product keeps from splashing about on the sides and ruining yield and pH balance.

The product in (9 inch×12 inch pan) was placed in a vacuum oven set at 230° C. with a 7 CFM vacuum pump attached. After 45 minutes, the 532 g of product suffered a weight loss of 25 g after 30 minutes. Another 30 minutes resulted in 8 g weight loss. Another 30 minutes resulted in 2 g weight loss. When 6 g of the resultant DETAPPA were dissolved in 20 ml water, 7 ml syrup resulted indicating high molecular weight. The pH of the product was approximately 4.2 to the accuracy of pH paper, unchanged from the pH initial low molecular weight product.

Experiment 1255 was repeated with this condensed EAPPA product experiment 105. There was not any observable difference with the previous product using the product from Example 1.

Example FR nylon: A composition containing 20% of EAPPA condensed experiment 105 and 80% nylon 66 extruded perfectly in a twin screw extruder with no sign of degradation. The product without condensation would not extrude without severe degradation of the FR nylon composition.

Experiment 115—water: 180 g of DETA mixed with 180 g water and 360 g of PPA 115% were added to the pressure cooker. The pressure cooker and hot plate were at 0° C., as the experiment was performed in a freezing room with no heat. The hot plate setting is such that the temperature of the hot plate will reach a temperature of 170° C. but will take about 30 minutes. The mixing and the hot plate are started simultaneously. The EA/water and PPA 115% start reacting after about 2 minutes as some steam begins to leak out. The reaction went to completion and the final temperature was about 120° C. The product is much less viscous. The product was dried in vacuum oven at 150° C. for two hours. The product did not form syrup when dissolved in water indicating low molecular weight. It is expected that molecular weight will be adversely effected when an aqueous solution of EAPPA is subjected to 150° C. for 60 minutes. The EAPPA samples in U.S. Pat. No. 8,212,073 and us2006/0175587 made with commercial PPA performed poorly in extrusion, because they were made with water, which adversely effected their properties. The presence of water in a composition at high temperature has bad effect on molecular weight. This composition can be converted to acceptable quality by condensation but more difficult.

Experiment 115: 180 g of DETA and 360 g of PPA 115% were added to the pressure cooker. The pressure cooker and hot plate were at 0° C., as the experiment was performed in a freezing room with no heat. The hot plate setting is such that the temperature of the hot plate will reach a temperature of 170° C. but will take about 30 minutes. The mixing and the hot plate are started simultaneously. The EA and PPA 115% start reacting after about 2 minutes as some steam begins to leak out. The pot was still cold indicating not much exothermic heat generated. Then the mixer freezes and stops mixing. The pot is still cold to the touch. The belts powering the mixer start slipping instead of mixing. Upon opening the pressure cooker, liquid pool of DETA was observed as well as pool of PPA 115. There is a large chunk of EAPPA that has frozen the mixer. The pH of the chunk was uneven but in the range of 2, a very undesirable product. Thus, this in an example of incomplete reaction very different than with PPA 105.

Experiment 115 completed to form DETAPPA: The pressure cooker with contents were allowed to sit for two days at nearly 0° C. There was no further reaction between pools of DETA and PPA 115 and low pH DETAPPA115. The large chunk of EAPPA was broken into small pieces so that the mixing element could spin. The hot plate was heated to 100° C. and the mixer was turned on. This time the reaction between DETA, PPA 115, and the broken up EAPPA progressed rapidly with much heat given off. The temperature of the pot now reached 200° C. After 10 minutes, the pot was removed and allowed to cool. It was unexpected that the reaction completed without there being a devise to wipe off the sides of the reactor during mixing, a result of very high boiling points the probable reason. The yield was to close to theoretical yield. Four g of DETAPPA115 yielded 3 ml of syrup when dissolved in 15 ml water. The pH was 4.0. The product was subjected to full vacuum at 230° C. The weight loss was 1.7%, much smaller than for DETAPPA105. The pH was still 4.0. This product dissolved in 15 ml water and yielded 4.5 ml syrup for 4 g product.

Experiment 117: Experiment 115 was repeated with PPA 117% and the results were identical and possibly less reaction occurred before the mixer froze. The observable difference was that the weight loss during condensation to raise molecular weight was less than 1%. It was unexpected that the reaction completed without there being a devise to wipe off the sides of the reactor during mixing, a result of very high boiling points the probable reason.

Weight loss during condensation is greatest for EAPPA compositions made with PPA 105%. The weight loss is least for EAPPA made with PPA 117%. The weight loss is due to water loss, which was collected by condensation of off gas from vacuum oven before the gas reached the vacuum pump.

The outcome for experiment 115 and 117 would be expected to be different had a high intensity mixer been used. The low pH DETAPPA would be pulverized as formed and continues to mix with the remaining DETA. There would be no need to stop the reaction and break up the large pieces. Eventually, the combination of external heating and exothermic heating would cause the DETA, PPA, and EAPPA to completely react and melt.

The product could be used as is or could be subjected to vacuum temperature condensation to reduce the small amount of ortho and pyrophosphate content. A person knowledgeable in this chemistry could easily determine the process, which will depend on the equipment. The preferred equipment is a high speed mixer powerful enough to pulverize, attain a temperature of 250° C., and is air tight so that vacuum heating at high temperature can be applied upon completion of reaction and the product is still hot. It is further preferred that the high intensity mixer has a breaker bar to break up balls of product that are incompletely reacted.

An advantage of PPA 105% over PPA 115% and PPA 117% is lower temperature for reaction, easy to handle at room temperature if a proper mixer not available. The product is easily upgraded to higher molecular weight via vacuum temperature condensation. It is well documented that the orthophosphate amine compounds have lower thermal stability than their polyphosphate versions. All PPA grades have some orthophosphate content with grade 117% having 3% and grade 115% having 5%. For polymer applications, it is preferred to vacuum temperature treat all EAPPA even if made with high molecular weight grade 117% in order to decrease the amount of monophosphate content. Heat treating always results in higher molecular weight, vacuum quickens the process. The higher overall molecular weight of EAPPA compositions is obvious from the increase in viscosity that vacuum temperature causes. It is preferred to exclude air from the reactions so to exclude reactions with air and moisture in air.

The flame retardant containing polymer composition is found to be plasticized by the addition of moisture. If a flame retardant containing composition is placed in a humidity chamber, a few per cent moisture is absorbed. The elongation of the flame retardant containing composition will be increased. Because the elongation is increased, the tensile strength is increased because the sample breaks at a greater elongation as the stress strain curve is pretty much unchanged by the absorption of water.

Moisture Example: A sample of example 1255 is placed in a humidity chamber for 12 hours. The humidity chamber is created by setting the temperature in a vacuum oven at 65° C., placing a pan of water in the vacuum oven closing the door tight but not using vacuum. The sample of example 1253 subjected to such humidity treatment had its elongation and tensile strength increase by over 30%.

Example Lubricant: A composition was formed in a Brabender consisting of 184 g of DETAPPA 115%, 46 g FP2100J 104 g Elvax 260, 11 g Elvaloy PTW, and 2 g EPON 828. The composition appeared brittle in that 0.25 inch plaques could not be bent 270 degrees or more without breaking. This composition was put back into the Brabender and 1% of Mobil One synthetic grease was added. The sample was very flexible in that 0.25 inch plaques could be bent a full 360 degrees without breaking. Next, plaques were placed in a vacuum oven, door closed, at 85° C. and a tray of water which than becomes a humidity chamber. Plaques with the grease lubricant were placed in the chamber for 16 hours. The samples did not become sticky. The samples gained less than 1% by weight water where normally about 5% water by weight would be gained in this humidity chamber experiment.

The experiment was repeated with EPON 1007F for EPON 828 with same results. The lower water uptake is of huge importance for electrical applications.

Example EAPPA Solution: Dissolve DETAPPA of example DETAPPA105% in water so that the concentration by weight is 600% water.

Example 1016a: 130 g of dried sawdust is mixed with 96 g of EAPPA solution and dried at 68C and vacuum of 28 inches Hg was dried for four hours.

Example 1016l: In a Brabender at 173C, 23 g of PP, 7 g of Elvaloy PTW are mixed with 34 g of Example 1016a. A plaque is formed in a hot press. The plaque does not ignite when subjected to a UL94 test flame.

Example 1017l: In a Brabender at 173C, 23 g of PP, 7 g of Elvaloy PTW are mixed with 34 g of Example 1016a. A plaque is formed in a hot press. The plaque does not ignite when subjected to a UL94 test flame.

Examples 1016l and 1017l appear to be attractive wood plastic composites (WPC). A thin film or layer of Surlyn was added to the surface WPC and good adhesion was found. A best practice is for the Surlyn to contain a flame retardant.

Example 117Bad: On a 28mm twin screw a composition was extruded: Example 1 DETAPPA 30.6%, FP2100J 10.2%, Bayer Desmopan 385ES 48.9%, Styrolutions Elastollan C85A10 6.3%, Elvaloy PTW 3.0%, and Honeywell Aclyn 201 1%. This sample extruded very poorly for the intended FR loading of 40.8%. This result suggests that DETAPPA of Example 1 was problematic at high loading and requires condensation to increase the molecular weight and thermal stability.

Example Plenum: Example 1 DETAPPA 51.8%, fp2100J 14%, Synfluid 150 0.8%, Aerosil r972 1.2%, Elvax 260 23.2%, ateva 1231 5.8%, elvaloy ptw 3.2%. This sample extruded poorly. The DETAPPA from Example 1 was subjected to condensation by heating in a vacuum oven for 60 minutes at 250° C. The sample extruded perfectly. The polymer was then used to make 1500 ft. of communication cable consisting of 8 PE coated conductors and covered by a jacket at 30 mil thickness, using a small single screw wire coater.

Example Plenum AC400: The composition example plenum with condensed DETAPPA from example 1 was repeated but with Honeywell AC400 substituted for Synfluid 150. This sample would not extrude well on a twin screw extruder. The lubricant Synfluid 150 is thus superior lubricant to AC400 for this composition.

Example Plenum Result: The cable of example plenum is subjected to UL communication cable plenum test UL 910. The cable passes that test.

Example Nylon Fiber: A composition was extruded on a twin screw consisting of 80% Nylon 66 and 20% condensed DETAPPA that had undergone a pretreatment with Synfluid at a ratio of 1.92 g condensed DETAPPA to 0.03 g Synfluid 150. The strand was very flexible and could be run to a very small diameter by running the extruder at a low rate suggesting that a fiber could be made. This suggests than this resin could be then added to a single screw spinning machine to make nylon fiber containing over 19% DETAPPA flame retardant. Such small diameter nylon was collected to make a crude yarn with cotton.

Example PET Fiber: A composition was extruded on a twin screw consisting of 80% PET and 20% condensed DETAPPA that had undergone a pretreatment with Synfluid at a ratio of 1.92 g DETAPPA to 0.03 g Synfluid 150. The strand was very flexible and could be run to a very small diameter by running the extruder at a low rate suggesting that a fiber could be made.

Example PP Fiber: A composition was extruded on a twin screw consisting of 77% polypropylene, 3% Elvaloy PTW, and 20% DETAPPA that had undergone a pretreatment with Synfluid at a ratio of 1.92 g DETAPPA to 0.03 g Synfluid 150. The strand was very flexible and could be run to a very small diameter by running the extruder at a low rate suggesting that a fiber could be made. The limited oxygen index (LOI) is 31% oxygen, which exceeds that of Nomex, which is 27-28.

Example Flame Retardant Nylon/Cotton Yarn: The thin diameter strand of example nylon fiber was cut into 1.5 inch lengths to make crude staple. This crude staple was fashioned into a cylindrical shape and burned with a cigarette lighter for 10 seconds. The sample charred but melted as well. Next the crude FR nylon staple was mixed with cotton with in equal amounts and shaped into a cylinder to resemble a crude yarn. A cigarette lighter was applied for 10 seconds. The sample charred as the cotton burned away.

However the sample did not melt but went to char and retained its shape. It is expected that the same result will hold for real yarn where the density is much higher and much lower open surface. This yarn seems to have passed one of the requirements of protective garments is that little or no melting when a flame is applied.

Example Wildfire: Put a thin coating of EAPPA solution (60% concentration by weight with water) onto a ¼" wooden dowel and let dry in air to remove substantial water. Apply torch to coated dowel suspended vertically for two minutes. The flame goes out almost immediately. A thin crust formed on the surface that protected the interior. The crust was found to protect the dowel and no burning embers formed and the fuel load was reduced as most of the dowel is not consumed by the fire. The dowel burns with a very small flame indicating a slow burn rate, which is crucial to stopping a fire. After a long time (about 10 minutes), the interior where the flame is applied becomes hollow. The char does not burn through so an ember can form. This experiment demonstrates: The solution on the dowel stopped burning embers, reduced the fuel load and reduced the fuel consumption rate to minimize the heat flux emitted essential for the fast progression of forest fires. A comparable solution formed by adding water, PPA and DETA together in a direct reaction had much more dripping from the dowel making it less effective and was abandoned. It was also apparent that the EAPPA solution exhibited more intumescense in this dowel experiment than the syrup of U.S. Pat. No. 8,703,853. The extra intumescense gave better performance by weight retained. The above experiment was repeated with a 75% concentration. The surface char is noticeably thicker, slower burning, smaller flame, and no embers or heat flux. That higher concentrated EAPPA solutions can now be prepared is a big advantage of these new EAPPA's.

For comparison, the torch is applied to an untreated dowel 0.25 inch thick for two minutes, with dowel being vertical in both experiments. The dowel continues to burn with a large flame, about 3-4 inches long after the torch is removed. A lot of heat is now being radiated and continues to be radiated after the flame is removed. Thus the coating has reduced the emitted heat flux by well over 50%. This property that wood surfaces wetted with EAPPA solutions prevent ember formation, lower burn rate, and surface temperature, and heat released was not disclosed in U.S. Pat. No. 8,212,073.

Example: Comparison and differentiation of aqueous DETAPPA made with commercial PPA 115%, by two methods:

1). Following procedure of U.S. Pat. No. 8,212,073, 250 g of PPA 115% was placed in aluminum pan. 170 g of DETA and 145 g of water were mixed together and then added to the pan. PPA 105% had been used in U.S. Pat. No. 8,212,073. Some DETA and water escaped due to substantial heat release as the solution became very hot and the reactor was open to air as practiced in U.S. Pat. No. 8,121,073. An aqueous solution was formed but no syrup separated to the bottom as if it had been prepared with low molecular weight PPA 105. It was expected that the high temperature of the solution and acidity during formation and extended time cooling in presence of water would have had a detrimental effect on molecular weight, as evidenced by lack of a syrup phase separating. The pH was 3.2 indicating a large amount of DETA/water escaped. This aqueous solution was allowed to stand for a year, the molecular weight was substantially degraded and the metal paint can started to leak.

2). Following the method of this invention, 250 g of PPA 115% and 125 g of DETA were reacted anhydrously in a closed reactor to prevent loss of DETA as the temperature reached nearly 195° C. The reactor is sized so that the pressure is not too high, so that unwanted side reactions do not occur and explosive conditions avoided. The pressure generated has to be less than the pressure the reactor is qualified for. A reactor about 3 L seems to work well here for batch size 375 g. Because the reactor volume is large and the sides are not scrapped, regions of differing compositions could have segregated. The stickiness of the product was probably important in obtaining a single phase EAPPA provided that the temperature is high enough for all ingredients to melt together and mixing intense enough. Vacuum condensation was not applied to raise molecular weight and remove the less desired low molecular weight content. The high temperature could have led to unwanted reactions/decompositions that could have led to bad results. Fortunately, the desired product formed despite the high temperature from exothermic reaction. The absence of water is important so as not to provide a pathway to loss of molecular weight or side reactions.

After the DETAPPA115 solidified and cooled to room temperature, 11 g water was added per 7 g DETAPPA 115 and a 15 ml viscous solution (pH about 4.3) was formed which was one phase, a concentration of 39%. The solution was quite dense further indicating a much higher molecular than in previous example. If another 10 g water is added, a two phase solution forms, 12 ml of the more dense and 13 ml of lower molecular weight. If 11 g water is added to 7 g of DETAPPA117, a two phase solution formed that is 12 g higher molecular weight and 3 g lower molecular weight. The same happened if DETAPPA115 is subjected to condensation and then dissolved in water at a ratio of 7 g product/11 g water. The 15 ml solution is two phase: 12 ml of higher molecular weight and 3 ml of lower molecular weight. Thus, the formation of two phase solution is not directly related to quality for extrusion into polymers such as nylon. The two phase solution does appear to correlate with higher molecular weight.

The higher molecular weight product obtained anhydrously is desirable for the wildfire application so that the DETAPPA aqueous solution will form very sticky film when applied to brush and branches of trees and further spread out to form a thicker protective film due to heat from approaching fire. The crop dusting equipment used to apply this solution sprays droplets onto fuel, and these droplets need to be very sticky and not drip off. Thus, it is preferred to mix DETAPPA from the anhydrous approach shortly before use so not to have any significant reduction in molecular weight. One can also add just enough water so that only one dense solution forms.

Thickness of the film is important. It is preferred dissolve in water EAPPA that has been condensed to higher molecular weight as it forms a thicker film that yields a thicker protective coating when exposed to a flame. Low molecular weight solution tends to drip off High molecular weight does not drip off but more difficult to spray. A film thickness of at least 1 mil is preferred and at least 3 mil is more preferred. Standard paint thickness is about 4 mil. It is preferred that at least 25% of fuel be wetted with the solution. More preferred is 33% and most preferred is 67% be wet with EAPPA solution. Depending viscosity requirement of the equipment, the viscosity can be varied over wide range by manipulating molecular weight and concentration. More than one coating may be necessary depending on flammability. At a thickness of 3 mil, it is found for a wooden dowel, the rate of burn and surface temperature above the burn are reduced by at least 25%. The heat flux is reduced by at least 50%.

Example Coated Dowel: A solution of 50% concentration (50 g DETAPPA 115% and 50 g water) was painted onto an 18 inch long dowel that is square with each side being ¼ inch. The dowel was weighed and the amount of DETAPPA was about 1 g. The thickness was calculated to be about 60 micron or 2.3 mil. When exposed to a propane torch, DETAPPA converted to a surface crust and the dowel burned very slowly, releasing heat very slowly, and flame slowly goes out as flame is unable to spread up the vertically held dowel as it does for uncoated. The torch was withdrawn after two minutes of application. The small flame goes out nearly at once and the surface temperature of the burned area was 90° F. (32° C.) within 1 minute and could be touched. The interior of the dowel converted to char where it was directly subjected to the propane torch, with Benzomatic TS4000 automatic lighter from Home Depot. An untreated dowel burned in the same way for two minutes continued to burn and formed embers and released much heat. Even for a single stick form of fuel, stopping embers with huge reduction in rate of heat flux output is readily apparent.

The weight of the coated dowel before and after burning was compared with the weight of uncoated dowel before and after burning. The weight loss difference indicates that the coating reduced the amount of heat (calories consumed) released by well over 50%. The heat flux at any time was also reduced by at least 50%, a key element to stopping a wildfire. A thinner coating on wildfire fuel would take a longer time to stop the fire. A coating of about 2 mil on wildfire fuel would be preferred for fuel that on average has a diameter of 0.25 inch. An uncoated vertical dowel (0.25 inch) continues to burn after the torch removed whereas the coated stops.

A very thin coating was applied to a dowel 0.25 inch by using a finger dipped into the DETAPPA solution. The dowel burned at very slow rate with no ember formation even though very little solution was applied, about 0.4 g as compared to about 1 g when brushed on. The surface crust is thinner as expected but still works.

Example Partial Coated Fuel: Next, 14 inches of a 18 inch long dowel were coated with the 50% concentration DETAPPA. The dowel is held vertically and the torch is applied to the uncoated end. The flame progresses upward and stops as it gets to the coated and becomes small and goes out. On this basis, it is concluded that not all the fuel needs to be coated.

Brush fire example of stopping embers and heat flux:
Six ft. metal poles and two 4 ft. wide roofing metal sheets 12 ft. long from Home Depot Inc. were used to create an enclosure 12 feet long with the sides three feet apart and open on two ends. The metal enclosure was to filled 2.5 ft. high with dry branches from dead trees for a realistic brush fire. On one side, 6 ft. long section of the dry branches were sprayed with a 50% solution of EAPPA made with DETA and PPA 115%. The coated branches were allowed to dry for 3 hours. The uncoated brush was ignited with a torch and allowed to burn. A large 2 ft high fan was stationed at the entrance to blow the flames and embers being created toward the coated branches. After about 5 minutes the flames became very intense and the heat flux was intense so that one could not stand near the fire. The temperature of the metal sheets exceeded 600° F. on the interior, the max temperature of our gauge. The emitted heat flux was intense. The coated branches appeared to undergo a very short ignition at which time a surface crust or char forms and their burning stopped. After about 10 minutes, the uncoated branches have burned and formed hot coals. The coated branches did not burn just charred over about 18 inches near the interface of coated/uncoated. The coals were swept under the coated branches. Still, the coated branches did not ignite and the emitted heat flux was nearly non existent, at least 75% reduction. This example shows that the coating stops the spread of the fire and should do likewise for a wildfire: the coated branches would not convert to embers or emit a lot of heat, both of which are necessary to stop a wildfire. By comparing the weight of the remains of coated brush that hardly burned and uncoated brush, the coating reduced the amount of heat (calories consumed) released by well over 50%. The heat flux at any time was also reduced by at least 50%, a key element to stopping a wildfire.

Example Cooking Oil: A 6 inch in diameter pan with 0.5 inch of cooking oil was heated with a gas stove and then ignited with a torch. An 80% concentration of condensed DETAPPA with water solution was sprayed onto the oil fire, which was quickly put out. There was no flaming from the water content as might occur if water is used as a flame retardant for an oil fire. The example was repeated. This time a powdered condensed DETAPPA was applied to the cooking oil fire, which went out immediately.

The same principles make EAPPA and EAPPA aqueous solutions effective tool to stop all fires including gas, structures, tires, etc.

Alternative EAPPA wildfire solution: In a closed vessel mix 200 g of PPA 105%, 100 g of DETA, and 150 g H2O, a 67% concentration which became hot and then cool in the vessel. The solution was allowed to stand for six months. The viscosity had gone down noticeably. When applied to a wooden dowel, the coating is very thin because there is little molecular weight due to decomposition. The resistance to flaming is now less than the freshly prepared and the intumescent coating is less. This result supports the idea that higher molecular weight EAPPA functions better in both plastics and fire extinguishing.

Example Corrosion: EAPPA syrup from that formed by ion exchange method in U.S. Pat. No. 8,212,073 was stored in standard metal paint can. Within two years time, the paint can started to leak the syrup due to corrosion. One of the requirements of the US forest service is that flame retardants for use on wildfires not be corrosive to metals. The forest service does not want to have the possibility of corrosion to metal tanks on fire fighting equipment or to metal drums that might store a liquid flame retardant for future use. The EAPPA either regular or condensed can be stored indefinitely as powders in moisture proof containers. These powders can be then be sprayed as is onto fires or mixed with water and then sprayed as needed. It is preferred to spray an aqueous solution in front of the fire if one wishes to stop a wildfire from progressing.

Example Transportation: It is less expensive to transport powdered form of EAPPA in moisture proof containers. Transportation of liquid form of EAPPA has more regulatory hurdles as well as being corrosive.

For gas fires, oil fires, chemical fires, tankers, airplanes, trains, and other contained fires, it is preferred to spray a powdered form of EAPPA directly onto the fire.

It was unexpected that the direct reaction of EA and PPA could be done directly and that the heat generated could be easily absorbed by the EAPPA product and container. It was unexpected that the temperature during synthesis of EAPPA could rise to 200° C. with no detrimental reactions observed. It is preferred that external heating be applied so that a temperature of at least 200° C. is maintained if condensation is applied. It is preferred that the reaction be performed moisture free. It is more preferred that the reaction of EA and PPA be performed in an inert atmosphere such as nitrogen. Contrary to findings in U.S. Pat. Nos. 7,138,443, 8,212,073, and 8,703,853, unexpectedly a new EAPPA composition and process has been found by using commercial PPA and EA's. In these US patents, it was claimed that suitable EAPPA for high temperature extrusion as in nylon 66 could be made only with IX process specifically excluding compositions made of commercial PPA. Here we show how to make EAPPA suitable for nylon 66 extrusion with commercial PPA and with less if any waste stream and at lower cost.

The findings in this specification are not reliant on any particular theory.
1. http://www.dow.com/amines/pdfs/108-01347.pdf
2. http://cameochemicals.noaa.gov/chemica/9000,
3. Masson, J -F., Energy & Fuels, Vol. 22, No. 4, 2008, pp. 2637-2640.
4. Shen, Chung Y., Ind. Eng. Chem., Process Des. Develop., Vol. 14, No. 1, 1975.

I claim:

1. A method for preparing sodium free ethyleneamine polyphosphate (EAPPA), the method comprising the step of reacting an ethyleneamine (EA) and polyphosphoric acid (PPA) without water or other solvent at a EA/PPA reaction ratio and at a reaction temperature so that the reaction of EA and PPA goes to completion, and wherein the EA/PPA ratio is operative such that the pH of a 10% aqueous solution by weight of the resulting EAPPA is in the range 2 to 7.5.

2. The method according to claim 1, further comprising the step of subjecting the resulting EAPPA to subsequent condensation.

3. The method to form sodium free ethyleneamine polyphosphate (EAPPA), as claimed in claim 2, wherein the condensation reaction of resulting EAPPA is such that thermo gravimetric analysis (TGA) weight loss of the EAPPA to 325° C. is less than 1% by weight, at a heating rate of 20° C. per minute in nitrogen atmosphere.

4. The method to form sodium free ethyleneamine polyphosphate (EAPPA), as claimed in claim 2, wherein the condensation reaction is such that 500 g sample of the resulting EAPPA with surface area at least 25 sq. in. subjected to heating under vacuum at a temperature between 200° C. and 250° C. has a vacuum pressure less than 20 Torr for at least 15 minutes, with the vacuum system able to attain vacuum pressure of less than 5 Torr.

5. The method to form sodium free ethyleneamine polyphosphate (EAPPA) of claim 1, wherein the reaction ratio of EA to PPA is at least 0.45 by weight of composition and the grade of PPA is PPA 105% to PPA 117%.

6. The method according to claim 1, wherein said step of reacting comprises mixing EA and PPA in a closed container and the final temperature sufficient is to melt the formed EAPPA composition.

7. The method according to claim 1 or 2, wherein the ethyleneamine is selected from the group consisting of ethylenediamine (EDA), diethylenetriamine (DETA), piperazine (PIP), triethylenetetramine (TETA), tetraethylenepentamine (TEPA), and pentaethylenehexamine (PEHA).

8. A method for preparing an aqueous solution, the aqueous solution comprises the sodium free EAPPA prepared according to the method of claim 1 or 2 at a ratio of at least 20% by weight.

9. The method for containing or fighting fires of claim 8 wherein said step of applying comprises spraying the aqueous solution on to surfaces of fuel in front of the fire in a quantity or form that is operative to wet at least 25% of the surface at a thickness of at least 0.25 mil.

10. The method for containing or fighting fires of claim 8 wherein the quantity or form of the aqueous solution is operative to wet wooden surface to stop the formation of embers and reduce the amount of heat released.

11. A method for decreasing the heat flux that a wood emits comprising coating the wood with the aqueous solution prepared according to the method of claim 8 at a thickness of the aqueous solution of at least 1 mil.

12. A method for preparing an aqueous solution comprising adding water and mixing after the reaction of EA and PPA goes to completion in the method of claim 1 or 2.

* * * * *